United States Patent [19]

Repta

[11] Patent Number: 4,663,349

[45] Date of Patent: May 5, 1987

[54] RECTALLY ABSORBABLE FORM OF L-DOPA

[75] Inventor: A. J. Repta, Lawrence, Kans.

[73] Assignee: Merck & Co., Inc., Rahway, N.J.

[21] Appl. No.: 814,861

[22] Filed: Dec. 30, 1985

[51] Int. Cl.$^4$ ............................................. A61K 31/24
[52] U.S. Cl. ..................................................... 514/535
[58] Field of Search ......................................... 514/535

[56] References Cited

PUBLICATIONS

*Cutting's Handbook of Pharmacology*, 41, "Sympathetic Stimulants of Adrenergic Agents", pp. 436–455, Sixth Edition (1979).

*The Merck Index*, pp. 3224 & 5314, Ninth Edition (1976).

*Primary Examiner*—Stanley J. Friedman
*Attorney, Agent, or Firm*—Manfred Polk; Michael C. Sudol, Jr.

[57] ABSTRACT

The invention relates to compositions and methods of enhancing rectal absorption of L-dopa via the formation of an ester prodrug and optionally with a decarboxylase inhibitor.

21 Claims, No Drawings

RECTALLY ABSORBABLE FORM OF L-DOPA

BACKGROUND OF THE INVENTION

The invention relates to compositions and methods of use of ester prodrug derivatives of L-dopa for enhancing absorption via rectal therapeutic application. More specifically, the invention relates to alkyl, aryl and substituted and unsubstituted aralkyl esters of L-dopa and their pharmaceutically acceptable counterion salts. Also, the heretofore disclosed compositions and methods may optionally include a decarboxylase inhibitor such as carbidopa and benserazide. The inhibitor serves three vital roles, namely, (1) prevents the breakdown of L-dopa, (2) reduces commonly know side effects, and (3) allows further expression of L-dopa pharmacological activity.

L-dopa is usually orally given with a L-amino acid decarboxylase inhibitor. Given in this fashion, L-dopa is effective in the treatment of Parkinson's disease. However, presumably due to erratic absorption and blood levels, control of disease symptoms is not always adequate. L-dopa esters have not provided significant advantages when given orally. This is probably due to ester hydrolysis in the g.i. tract and/or presystemic metabolism. These problems are ameliorated by the rectal route.

As employed in this application, the expression "prodrug" denotes a derivative of a known and proven prior art compound, which derivative, when absorbed into the bloodstream of a warm-blooded animal, "cleaves" in such a manner as to release the proven drug form and permits the same to afford improved therapeutic efficacy than that which could be obtained if the proven drug form, per se, was administered.

Also as employed in this application, the term "cleavage" denotes that the proven drug form is released and the remaining "cleaved" moiety is non-toxic and metabolized in such a manner that non-toxic, metabolic products are produced.

DESCRIPTION OF THE PRIOR ART

It is known to the art that dopa, L-dopa and dopamine, and their salts, are useful active agents for the treatment or management of a wide variety of disease states or conditions, e.g., they are useful anticholinergic agents, antiparkinsonian agents, adrenergic agents, cardiotonic agents, and the like. See generally Cutting's Handbook of Pharmacology, 41, "Sympathetic Stimulants of Adrenergic Agents", pp. 436-455, Sixth Edition (1979); The Merck Index, pp. 3424 & 5314, Ninth Edition (1976).

Nevertheless, it is also known to the art the sympathomimetic amines and various art-recognized therapeutically active derivatives thereof, are characterized by certain inherent disadvantages, notably serious bioavailability and physiological availability problems upon administration. Such reduced availability can be attributed in part to poor lipid solubility [by reason of the presence of the hydrophilic phenolic hydroxyl groups], and also to metabolic losses during and following conventional administration.

Also, it is further known to the art that L-dopa, following oral administration, undergoes extensive metabolism within the stomach and small intestine. Esters of L-dopa, when given orally, offer no advantage over L-dopa itself. Additionally, certain portions of the patient population experience extreme difficulty in swallowing oral formulations.

SUMMARY OF THE INVENTION

The invention relates to compositions and methods of enhancing rectal absorption of ester prodrug derivatives of L-dopa, specifically, the alkyl, aryl and substituted and unsubstituted aralkyl esters thereof and their pharmaceutically acceptable counterion salts. Optionally, said compositions and methods may include a decarboxylase inhibitor such as carbidopa and benserazide. Thus, there exists a need for an absorbable form of L-dopa which can be administered by an alternative route (other than oral), and which results in therapeutically effective plasma levels of L-dopa.

Accordingly, a major object of the invention is to provide an absorbable form of L-dopa for rectal application.

Another object of the invention is to provide a prodrug form of L-dopa which is characterized by enhanced solubility, can be administered in standard pharmaceutical formulations to warm-blooded animals to elicit a systemic physiological or pharmacological beneficial effect, and which exhibits enhanced bioavailability and physiological availability.

Still another object is to provide L-dopa prodrugs which will elicit a more effective sympathomimetic response, at lower concentrations or dosage levels, than its parent molecules.

The L-dopa esters of the invention can be administered rectally (with or without a decarboxylase inhibitor) as a suppository device or other modes administration. Release and absorption of the drug and subsequent hydrolysis in the blood would yield L-dopa which would be available to exhibit its intrinsic pharmacologic effects.

Other objects, features and advantages of the invention will be apparent to those skilled in the art from the description of the invention which follows.

DESCRIPTION OF THE INVENTION

The invention relates to compositions and methods of enhancing the rate of absorption of a rectally administered prodrug form of L-dopa. The compositions comprise an effective amount of an ester form of L-dopa (prodrug) and optionally a decarboxylase inhibitor such as carbidopa and benserazide formulated with commonly employed pharmaceutically acceptable excipients. The method generally comprises administering a dosage form capable of being rectally administered, wherein said dosage form comprises a therapeutically effective amount of L-dopa in a sufficient quantity to be effective in enhancing rectal absorption rates. The L-dopa prodrug ester derivatives of the invention are best described by the general formula below:

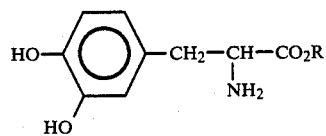

wherein R is a straight or branched chain alkyl($C_1$–$C_{20}$) such as methyl, ethyl, t-butyl, pentyl myristyl, palmityl and the like; aryl($C_6$–$C_9$) such as phenyl, tolyl and the like; substituted and unsubstituted aralkyl($C_7$–$C_{20}$) such as benzyl, alkoxybenzyl($C_8$–$C_{14}$) [methoxy, ethoxy, isobutoxy and the like], phenylethyl, phenylpropyl, phenylisobutyl, phenylhexyl, phenyloctyl and the like and pharmaceutically acceptable organic or inorganic counterion salts.

The synthetic processes for preparing the esters of L-dopa and the salts thereof are known in the art and are hereby incorporated herein by reference, namely, U.S. Pat. Nos. 3,891,696 and 4,035,507 and Journal of Pharmaceutical Sciences, 62, p. 510 (1973). For rectal application, the formulations may be prepared as microenemas, suppositories, rectal tablets, rectal devices, sustained-release formulations, and other standard procedures known in the art. The preferred formulation is a solid suppository comprising a pharmacologically required dose of the prodrug that is sufficient to provide therapeutic plasma levels of L-dopa, and sufficient suppository base to formulate an acceptable composition. The methods and choice of excipients and suppository bases are well known to those skilled in the art and the composition of said formulations is not limited to solid suppositories by this invention.

Generally, the amount of active agent employed in the practice of the invention ranges from 200 mg to 2.5 grams per day. Optionally, a decarboxylase inhibitor may be included at 1/10 to ¼ ratio of the amount of active agent. The percentage of pharmaceutically acceptable excipients employed herein can range from 55% to 95% of the total composition weight.

The following examples illustrate preparation of various compositions of the invention. The examples should be construed as illustrative rather than limitations thereof.

EXAMPLE 1

Aqueous microenemas (250 μl) containing either 2.0 mg L-dopa or 2.66 mg L-dopa ethyl ester HCl (equivalent to 2.0 mg L-dopa) were prepared. The solutions were adjusted to pH 5.5 and contained 0.02% ascorbic acid to prevent oxidation. Blood samples were collected following rectal administration to anesthetized rats, and plasma L-dopa determined by HPLC. The results, shown below, indicate significantly higher plasma levels of the L-dopa were obtained with the L-dopa ethyl ester HCl formulation.

| Time of Plasma Sample (min.) | Rat Plasma L-dopa (μg/ml) (mean ± S.D., n = 3) | |
| --- | --- | --- |
| | Rectal L-dopa | Rectal L-dopa ethyl ester HCl |
| 0 | N.D.[a] | N.D. |
| 15 | 0.02 ± 0.02 | 0.27 ± 0.04 |
| 30 | 0.02 ± 0.01 | 0.20 ± 0.08 |
| 60 | 0.01 ± 0.001 | 0.08 ± 0.01 |
| 90 | 0.01 ± 0.01 | 0.05 ± 0.01 |
| Percent L-dopa Bioavailability[b] | 1 | 12 ± 2.4 |

[a]N.D. = not detectible
[b]Percent bioavailability calculated versus 2.0 mg L-dopa given by i.v. injection

EXAMPLE 2

The experimental conditions of Example 1 were repeated, except that each formulation also contained 0.5 mg carbidopa, a decarboxylase inhibitor which is included to decrease L-dopa metabolism. The results, shown below, indicate a significant increase in plasma L-dopa levels and L-dopa bioavailability from the L-dopa ethyl ester HCl formulation (in the presence of carbidopa).

| Time of Plasma Sample (min.) | Rat Plasma L-dopa (μg/ml) (mean ± S.D., n = 3) | |
| --- | --- | --- |
| | Rectal L-dopa and Carbidopa | Rectal L-dopa ethyl ester HCl and Carbidopa |
| 0 | N.D.[a] | N.D. |
| 15 | 0.06 ± 0.03 | 0.76 ± 0.24 |
| 30 | 0.11 ± 0.07 | 1.00 ± 0.56 |
| 60 | 0.11 ± 0.05 | 0.60 ± 0.39 |
| 90 | 0.13 ± 0.10 | 0.36 ± 0.22 |
| Percent L-dopa Bioavailability[b] | 9 ± 5.5 | 62 ± 32.7 |

[a]N.D. = not detectible
[b]Percent bioavailability calculated versus 2.0 mg L-dopa given by i.v. injection

EXAMPLE 3

Aqueous formulations (pH 5.5, 0.1% ascorbic acid, 1.0 ml) containing 66.5 mg L-dopa ethyl ester HCl (equivalent to 50 mg L-dopa) were prepared for administration to Beagle dogs. Each dog received the rectal formulation following a 3-day pretreatment with oral carbidopa (25 mg b.i.d.). Blood samples were collected for 360 minutes and plasma L-dopa levels determined by HPLC. It is known that L-dopa itself is not significantly absorbed in dogs when administered by the rectal route. In the present studies, the bioavailability of L-dopa from the L-dopa ethyl ester HCl formulation was 34±25.4%, n=4. This represents a significant increase in plasma drug levels due to the application of the ester described in the instant application.

What is claimed is:

1. A method of enhancing the rate of absorption of a rectally administered composition comprising rectally administering to a patient a therapeutically effective dosage amount of an ester of L-dopa having the structural formula:

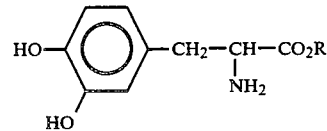

wherein R is alkyl($C_1$–$C_{20}$), aryl($C_6$–$C_9$), unsubstituted aralkyl($C_7$–$C_{20}$) or pharmaceutically acceptable organic or inorganic counterion salts and pharmaceutically acceptable excipients.

2. The method of claim 1, wherein R is alkyl.

3. The method of claim 2, wherein said alkyl is selected from the group consisting of methyl, ethyl, isopropyl, pentyl, myristyl and palmityl.

4. The method of claim 3, wherein said alkyl is ethyl.

5. The method of claim 1, wherein R is aryl.

6. The method of claim 5, wherein said aryl is selected from the group consisting of phenyl and tolyl.

7. The method of claim 6, wherein said aryl is tolyl.

8. The method of claim 1, wherein R is substituted and unsubstituted aralkyl.

9. The method of claim 8 wherein said aralkyl is selected from the group consisting of benzyl, alkoxybenzyl($C_8$–$C_{14}$), phenylethyl, phenylpropyl, phenylisobutyl and phenyloctyl.

10. The method of claim 9, wherein said aralkyl is phenylethyl.

11. The method of claim 1, wherein said ester of L-dopa is in microenema or suppository form.

12. A pharmaceutical composition for enhancing rectal absorption of L-dopa by administering a formulation comprising a therapeutically effective dosage amount of an ester of L-dopa of the structural formula:

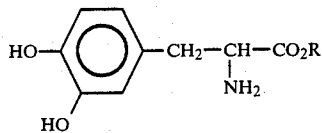

wherein R is alkyl($C_1$–$C_{20}$), aryl($C_6$–$C_9$), unsubstituted aralkyl($C_7$–$C_{20}$) or pharmaceutically acceptable organic or inorganic counterion salts and suppository base or microenema excipients.

13. The composition of claim 2, wherein R is alkyl.

14. The composition of claim 3, wherein said alkyl is selected from the group consisting of methyl, ethyl, isopropyl, pentyl, myristyl and palmityl.

15. The composition of claim 14, wherein said alkyl is ethyl.

16. The composition of claim 12, wherein R is aryl.

17. The composition of claim 16, wherein said aryl is selected from the group consisting of phenyl and tolyl.

18. The composition of claim 17, wherein said aryl is tolyl.

19. The composition of claim 12, wherein R is substituted and unsubstituted aralkyl.

20. The composition of claim 19, wherein said substituted and unsubstituted aralkyl is selected from the group consisting of benzyl, alkoxybenzyl($C_8$–$C_{14}$), phenylethyl, phenylpropyl, phenylisobutyl and phenyloctyl.

21. The composition of claim 20, wherein said aralkyl is phenylethyl.

* * * * *